(12) United States Patent
Schneider

(10) Patent No.: US 8,491,515 B2
(45) Date of Patent: Jul. 23, 2013

(54) PROSTHETIC SLEEVE

(75) Inventor: Scott Schneider, Wiesbaden (DE)

(73) Assignee: Otto Bock Healthcare GmbH, Duderstadt (DE)

(*) Notice: Subject to any disclaimer, the term of this patent is extended or adjusted under 35 U.S.C. 154(b) by 830 days.

(21) Appl. No.: 12/236,155

(22) Filed: Sep. 23, 2008

(65) Prior Publication Data

US 2010/0076357 A1     Mar. 25, 2010

(51) Int. Cl.
    *A61F 13/06*     (2006.01)
(52) U.S. Cl.
    USPC .................. 602/62; 602/60; 602/63
(58) Field of Classification Search
    USPC ............ 602/20, 23, 26, 60–63; 623/32–36, 623/57; 264/222; 425/2; D24/190–192
    See application file for complete search history.

(56) References Cited

U.S. PATENT DOCUMENTS

| | | | | |
|---|---|---|---|---|
| D265,248 S | * | 6/1982 | Grigorieff | D24/190 |
| 4,822,371 A | * | 4/1989 | Jolly et al. | 623/32 |
| D322,675 S | * | 12/1991 | Ross | D24/190 |
| 5,888,216 A | | 3/1999 | Haberman | |
| 5,897,517 A | * | 4/1999 | Laghi | 602/62 |
| 6,149,690 A | * | 11/2000 | Belzidsky | 623/32 |
| 6,406,499 B1 | | 6/2002 | Kania | |
| 6,790,238 B1 | * | 9/2004 | Martin | 623/36 |
| 6,869,560 B1 | * | 3/2005 | Drouin et al. | 264/500 |

* cited by examiner

*Primary Examiner* — Patricia Bianco
*Assistant Examiner* — Camtu Nguyen
(74) *Attorney, Agent, or Firm* — Holland and Hart LLP

(57) ABSTRACT

The invention is a sleeve for application to a human extremity. The sleeve has a tubular structure with distal and proximal openings, a pre-flexed section between the openings, and distal and proximal contact zones on opposing sides of the pre-flexed section. At least the distal contact zone extends from the pre-flexed section in a conically tapering manner. A distal end zone is disposed between the distal contact zone and the distal end. The distal end zone may also be conically tapered toward the distal end, and in one embodiment has a different degree of taper that the distal contact zone.

18 Claims, 2 Drawing Sheets

PROSTHETIC SLEEVE

FIELD OF THE INVENTION

The invention relates to a sleeve for application to a human extremity, more particularly, to a residual limb coupled to a prosthetic device.

BACKGROUND

Conventional prosthetic liners are worn between and/or over a human extremity and a prosthesis component such as a rod, pylon or socket. Such liners form an intermediate layer between the prosthesis and the extremity, and usually have a tubular construction with a closed, distal end. The liners adhere to the extremity on one side and to the inner side of the prosthesis component on the other side. Prosthetic liners may also have a cushioning effect and can act as a seal over the extremity and/or prosthetic component.

SUMMARY

The invention is in one embodiment a sleeve for application to a human extremity. The sleeve has a tubular structure with distal and proximal openings, a pre-flexed section between the openings and distal and proximal contact zones on opposing sides of the pre-flexed section. At least the distal contact zone extends from the pre-flexed section in a conically tapering manner. A distal end zone is disposed between the distal contact zone and the distal end. The distal end zone may also be conically tapered toward the distal end, and in one embodiment has a different degree of taper than the distal contact zone. In another embodiment, the distal end zone has a more significant or greater degree of taper than that of the distal contact zone. At least an inner surface of the sleeve may be formed from an elastomer layer designed to contact the extremity.

DETAILED DESCRIPTION

Figure 1:
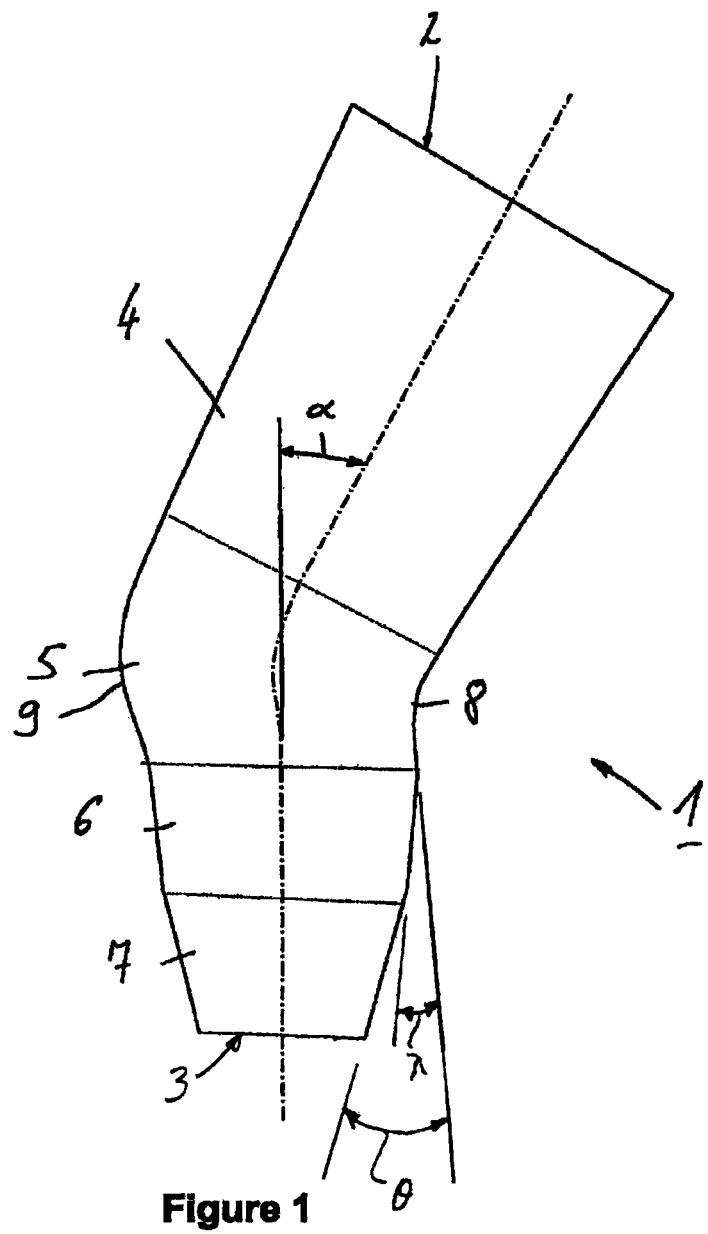
FIG. 1 is a schematic illustration of a prosthetic sleeve according to an embodiment of the present invention.

FIG. 1 shows a schematic side view of a prosthetic sleeve 1 having a tubular structure with a proximal open end 2 and a distal open end 3. The sleeve 1 also has a proximal contact zone 4, a pre-flexed section 5, and a distal contact zone 6. The distal contact zone 6 is directly adjacent to the pre-flexed section 5 and has a conical shape such that the diameter at the end adjacent the pre-flexed section 5 is larger than that of the end nearest to the distal opening 3.

Figure 2:
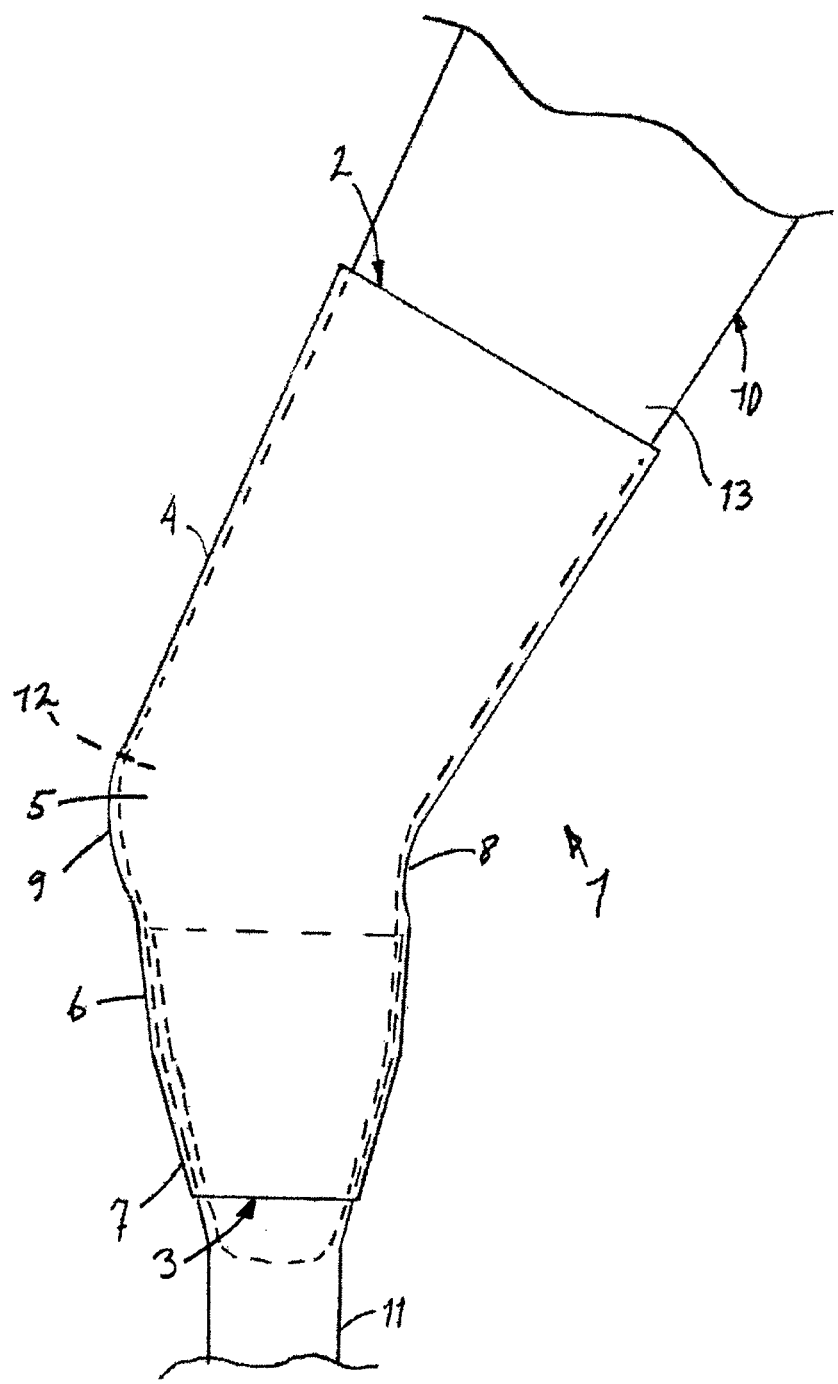
FIG. 2 is a schematic illustration of the prosthetic sleeve of FIG. 1 donned on a leg and prosthetic lower leg component.

An end zone 7 is directly adjacent to the distal end of the distal contact zone 6, and is also conically shaped so as to taper toward the distal opening 3. In one embodiment, the end section 7 has a more severe or significant degree of taper than the distal contact zone 6 to improve the contact of the sleeve 1 to a prosthetic component 11 (see FIG. 2).

In the illustrated embodiment, the sleeve 1 is configured to be donned on a leg 10 (see FIG. 2) such that the distal end zone 7 and possibly some or all of the distal contact zone 6 lies against a prosthetic lower leg component 11 to form a first seal, and the pre-flexed section 5 and proximal contact zone 4 lie against a knee 12 and thigh 13 of a wearer to form a second seal. A drawn-in section 8 lies on the flexor side in the region of the hollow of the knee 12 and a bulge 9 lies on the kneecap on the extension side. When the leg is flexed, the bulge 9 prevents pressure from being exerted on the kneecap. The drawn-in section 8 allows the sleeve 1 to stretch into the hollow of the knee 12, which reduces or prevents the sleeve material from bunching up and/or wrinkling. The bulge reduces or prevents the sleeve from being drawn too tightly over the relevant joint during flexion.

The pre-flexed angle $\alpha$, i.e., the angle that is formed between the central axes between the proximal and distal contact zones 4 and 6, is between 50 and 35°, more particularly, in the range of between 10° and 25°. The pre-flexed angle $\alpha$ corresponds to the natural flexion behavior of the extremity.

At least a portion, and preferably all, of outer side of the sleeve 1 may be covered with a textile, for example, a textile having a low coefficient of friction. This allows garments to be drawn over the sleeve 1 with reduced friction or sticking. It may also protect the underlying polymer material.

In one embodiment, the proximal contact zone 4 also has a slightly conical shape which widens toward the proximal opening 2 to a less severe or significant degree than the taper of distal end zone 7 and the distal contact zone 6. This reduces or prevents blood flow in the relevant extremity from being impeded. The distal end zone 7 may have a conical tapered shape with a first taper angle $\theta$. The distal contact zone 6 may have a conical tapered shape with a second taper angle $\lambda$. The first taper angle $\theta$ may be greater than the second taper angle $\lambda$. The tapered shape of the distal end zone 7 and the distal contact zone 6 are shown in FIG. 1 to each have a constant taper along an axial length thereof.

The prosthetic sleeve 1 of the present invention is particularly useful as a sealing sleeve, which can be pulled over a human extremity and a prosthesis component such as a prosthetic rod or cup to seal the transition zone between the prosthesis and the extremity. For embodiments configured to be secured over a natural or artificial joint. The distal contact zone 6 and distal end zone 7 may taper increasingly toward the distal end to provide a more secure connection at the distal end of the sleeve. If the distal end zone 7 lies at the outer side of a prosthesis rod, the prosthesis rod is held in place particularly securely, with minimal pressure being exerted on the tissue of the amputation stump.

Furthermore, the sleeve 1 is suitable for acting as an additional seal for prosthetic systems operating at low pressure. Such prosthetic systems remove air trapped between a prosthesis rod or receptacle and the amputation stump or a liner pulled over the stump. Air is removed using a vacuum pump and a valve, which forces the air out of the prosthesis rod during a pressure phase. The valve prevents the air from flowing back through the discharge opening. If a sealing sleeve is pulled over the prosthesis rod and the adjacent stump, it seals the interface between the prosthesis rod and the stump, or additionally the interfaces between the prosthesis rod, the liner and the stump. The low pressure may be maintained for a longer period of time using the sleeve, which decreases the likelihood of the rod moving. This gives the user of the prosthetic device a heightened feeling of security and increases acceptance of the prosthesis.

The invention claimed is:

1. A sealing sleeve sized and shaped for placement on a human extremity that is coupled to a prosthetic device to seal a transition zone between the human extremity and the prosthetic device, the sleeve comprising:

a flexible tubular structure including a distal opening and a proximal opening, a pre-flexed section between the openings, a distal contact zone and a proximal contact zone adjacent to, and on opposing sides of, the pre-flexed section, and a distal end zone between the distal contact zone and the distal opening;

wherein the distal contact zone and distal end zone conically taper toward the distal opening and extend over and form a first seal with an outer surface of the prosthetic device;

wherein the proximal contact zone forms a second seal against the human extremity;

wherein the distal end zone has a more significant taper than the distal contact zone; and wherein the flexible tubular structure includes an elastomer layer on an inner surface;

wherein the pre-flexed section has a bulge on an extension side, and wherein said bulge lies on a kneecap of said human extremity and said bulge prevents pressure from being exerted on said kneecap when said extremity is flexed.

2. The sleeve of claim 1 wherein the proximal contact zone conically tapers toward the pre-flexed section.

3. The sleeve of claim 1, wherein the pre-flexed section has a drawn-in section on a flexion side.

4. The sleeve of claim 1, further comprising a textile layer on an outer surface of the tubular structure.

5. The sleeve of claim 4, wherein the textile layer covers the entire outer surface of the sleeve.

6. The sleeve of claim 1, wherein the contact zones are pre-flexed in relation to each other at an angle of between 5° and 35°.

7. A sealing sleeve for sealing a transition zone between a human extremity and a prosthetic device, comprising:
  a flexible tubular structure including:
    a distal opening;
    a proximal opening;
    a pre-flexed section having a bulge on an extension side, and wherein said bulge lies on a kneecap of said human extremity and said bulge prevents pressure from being exerted on said kneecap when said extremity is flexed;
    a proximal contact zone arranged proximal of the pre-flexed section and configured to seal against the human extremity;
    a distal contact zone arranged distal of the pre-flexed section and having a conical tapered shape with a first taper angle;
    a distal end zone arranged distal of the distal contact zone and having a conical tapered shape with a second taper angle that is greater than the first taper angle;
  wherein at least one of the distal contact zone and distal end zone is configured to extend over and seal against an outer surface of the prosthetic device mounted to the human extremity.

8. The sleeve of claim 7, wherein the contact zones are pre-flexed in relation to each other at an angle of between 5° and 35°.

9. The sleeve of claim 7, wherein the flexible tubular structure includes an elastomer layer on an inner surface.

10. The sleeve of claim 7, wherein the proximal contact zone conically tapers toward the pre-flexed section.

11. The sleeve of claim 7, wherein the pre-flexed section has a drawn-in section on a flexion side.

12. The sleeve of claim 7, further comprising a textile layer on an outer surface of the tubular structure.

13. The sleeve of claim 12, wherein the textile layer covers the entire outer surface of the sleeve.

14. A flexible sealing sleeve for sealing a transition zone between the human extremity and the prosthetic device, comprising:
  a distal opening;
  a proximal opening;
  a pre-flexed section having a bulge on an extension side, and wherein said bulge lies on a kneecap of said human extremity and said bulge prevents pressure from being exerted on said kneecap when said extremity is flexed;
  a proximal contact zone arranged proximal of the pre-flexed section and configured to seals against the human extremity;
  a plurality of zones arranged distal of the pre-flexed section and having conical tapered shapes with different taper angles;
  wherein at least one of the plurality of zones arranged distal of the pre-flexed section are configured to extend over and seal against an outer surface of the prosthetic device mounted to the human extremity.

15. The sleeve of claim 14, wherein the taper angles of the zones arranged distal of the pre-flexed section increase moving toward the distal opening.

16. The sleeve of claim 14, wherein one of the zones arranged distal of the pre-flexed section is a distal contact zone arranged adjacent to the pre-flexed section.

17. The sleeve of claim 16, wherein another of the zones arranged distal of the pre-flexed section is a distal end zone arranged adjacent to and distal of the distal contact zone.

18. The sleeve of claim 14, further comprising an elastomer layer on an inner surface of the sleeve and a textile layer on an outer surface of the sleeve.

* * * * *